United States Patent [19]

Shields

[11] 4,310,763
[45] Jan. 12, 1982

[54] ELECTRO-OPTICAL ANALYZER FOR MEASURING PERCENTAGE BY WEIGHT OF FAT, PROTEIN AND LACTOSE IN MILK

[76] Inventor: John Shields, 23 North La., Wheldrake Nr. York, England

[21] Appl. No.: 84,662

[22] Filed: Oct. 15, 1979

[51] Int. Cl.³ .......................................... G01N 21/26
[52] U.S. Cl. .................................. 250/339; 250/343
[58] Field of Search ............... 250/339, 338, 340, 341, 250/343, 344, 345; 356/432, 433, 435, 436, 440, 441, 442

[56] References Cited

U.S. PATENT DOCUMENTS

| | | |
|---|---|---|
| 2,605,671 | 8/1952 | Canada . |
| 2,700,320 | 1/1955 | Malmros . |
| 2,764,097 | 9/1956 | Browne . |
| 2,819,402 | 1/1958 | Watson et al. . |
| 2,941,444 | 6/1960 | Frykman . |
| 3,161,768 | 12/1964 | Goulden . |
| 3,209,642 | 10/1965 | Mori et al. . |
| 3,250,174 | 5/1966 | Lutz . |
| 3,317,141 | 5/1967 | Mann . |
| 3,374,750 | 3/1968 | Hetz . |
| 3,435,209 | 3/1969 | Keahl . |
| 3,442,623 | 5/1969 | Aegidius . |
| 3,455,636 | 7/1969 | Haswell . |
| 3,552,864 | 1/1971 | Shields . |
| 3,819,276 | 6/1974 | Kiess et al. . |
| 3,819,277 | 6/1974 | Berthelot et al. . |
| 3,828,173 | 8/1974 | Knepler . |
| 3,878,727 | 4/1975 | Burns . |
| 4,037,970 | 7/1977 | Webster et al. . |
| 4,043,635 | 8/1977 | Siebert . |
| 4,076,983 | 2/1978 | Hopkins et al. . |
| 4,082,464 | 4/1978 | Johnson, Jr. . |
| 4,236,075 | 11/1980 | Nexo et al. .......................... 250/343 |
| 4,247,773 | 1/1981 | Nexo et al. .......................... 250/339 |

OTHER PUBLICATIONS

Milko-Scan Sales Literature, A/S N. Foss, Denmark, pp. 4–7.

*Primary Examiner*—Davis L. Willis
*Attorney, Agent, or Firm*—Barnes, Kisselle, Raisch & Choate

[57] ABSTRACT

Electro-optical apparatus for measurement of fat, protein, lactose and water or solids in milk wherein a milk sample is pumped by a homogenizer into an optical measurement cell. The specimen in the cell is then irradiated with reference and measurement beams at differing wavelengths for fat, protein, lactose and water respectively, and signals are stored indicative of uncorrected concentrations. A scaling and correction circuit includes cross-correction circuitry for compensating the effects on each reading caused by the other constituents. The signals so corrected are then provided in percentage by weight or weight over volume on suitable digital displays.

28 Claims, 16 Drawing Figures

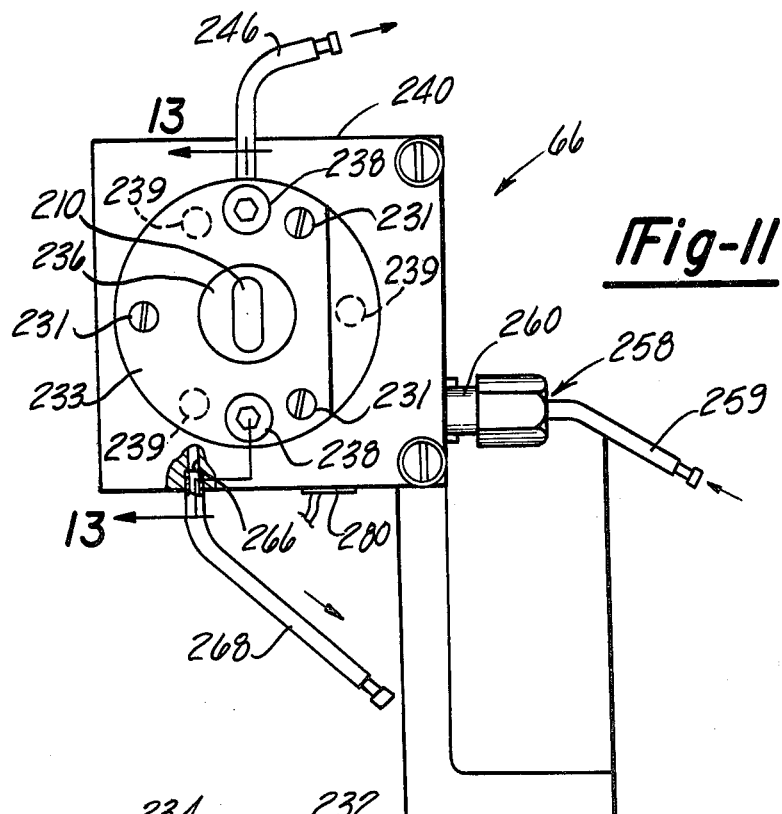
*Fig-11*
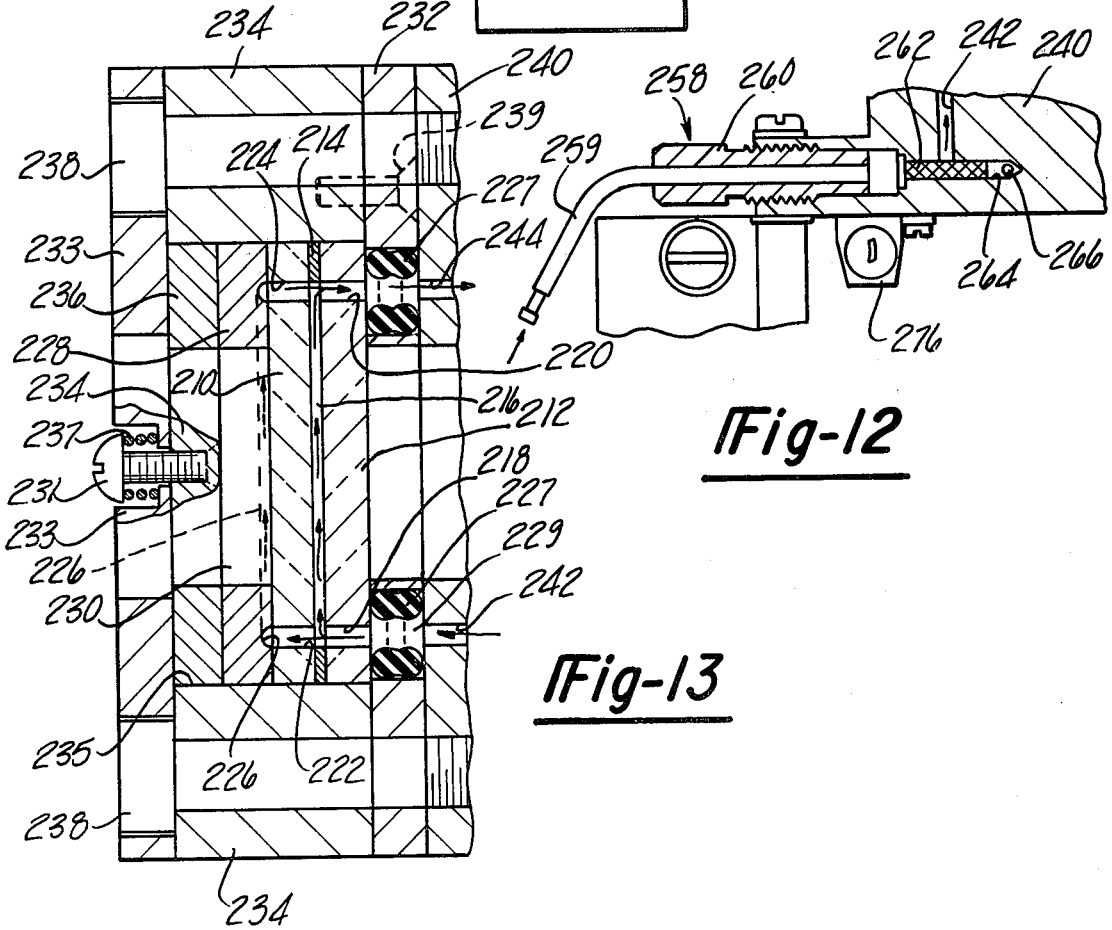
*Fig-12*
*Fig-13*

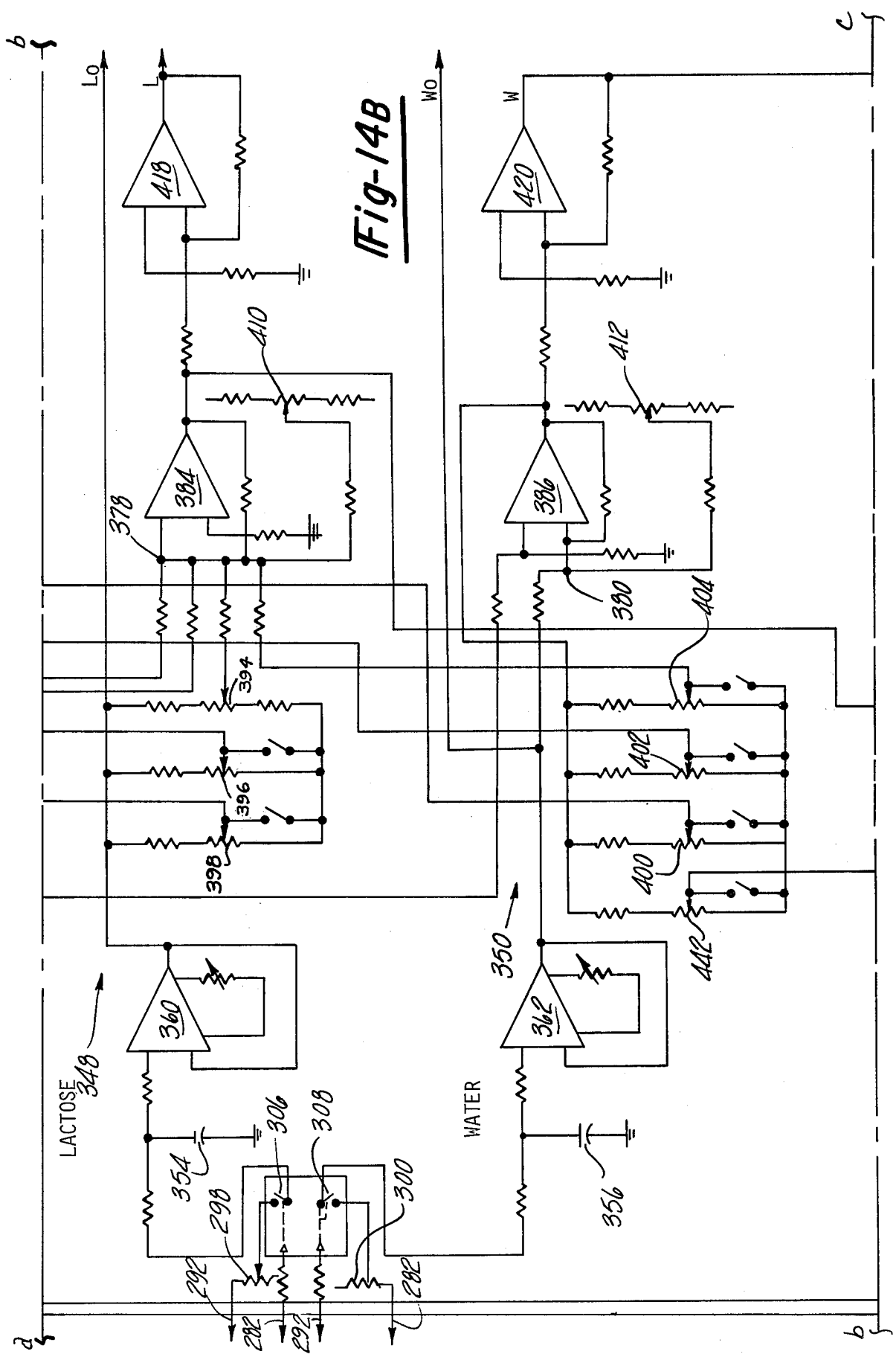

ELECTRO-OPTICAL ANALYZER FOR MEASURING PERCENTAGE BY WEIGHT OF FAT, PROTEIN AND LACTOSE IN MILK

The present invention is directed to spectrophotometric analysis, and more particularly to methods and apparatus for electro-optical analysis of emulsions and suspensions. Yet more specifically, the invention is directed to methods and apparatus for infrared analysis of percentage by weight of fat, protein and lactose in milk.

An object of the present invention is to provide a spectrophotometric analyzer for analysis of emulsions and suspensions which is economical in manufacture, and which is reliable and accurate over extended periods of operation. A further and more specific object of the invention is to provide a compact electro-optical analyzer possessing a reduced number of optical elements and a shortened beam path length as compared with prior art analyzers of similar type.

A further object of the invention is to provide an improved sample cell for spectrophotometric analysis of fluids. Yet another object of the invention is to provide an improved system and method for directing fluid to be analyzed to the sample cell.

In furtherance of the above, another object of the invention is to provide an improved homogenizer for use in optical analysis of emulsions and suspension such as milk.

The invention, together with additional objects, features and advantages thereof, will be best understood from the following description, the appended claims and the accompanying drawings in which:

FIGS. 9, 10 and 11 are respective plan, side elevational and front elevational views of the sample cell illustrated in FIG. 1 and schematically in FIG. 2;

Figure 3:
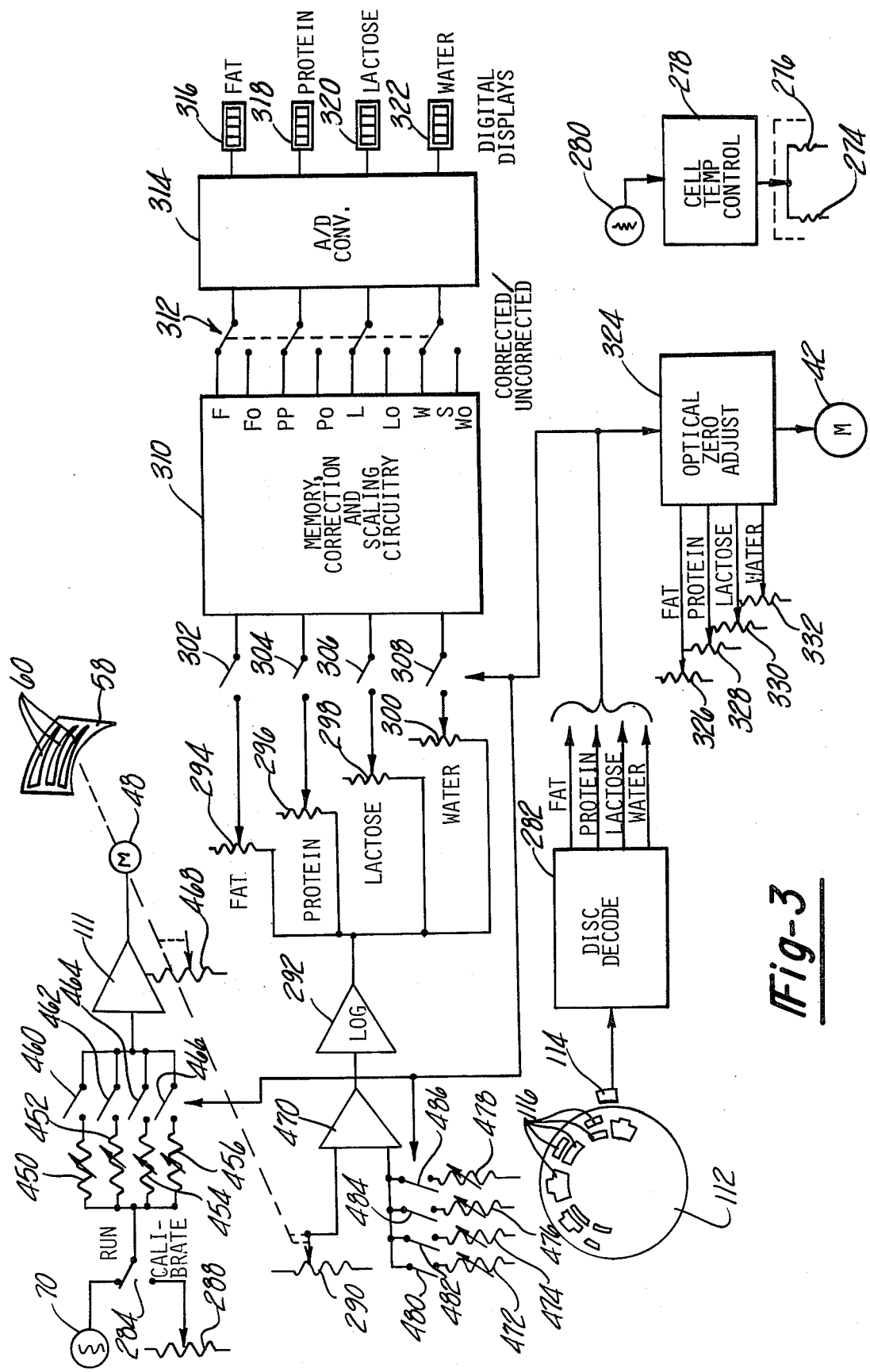
FIG. 3 is a functional block diagram of analysis electronics in accordance with the invention.
Figure 4:
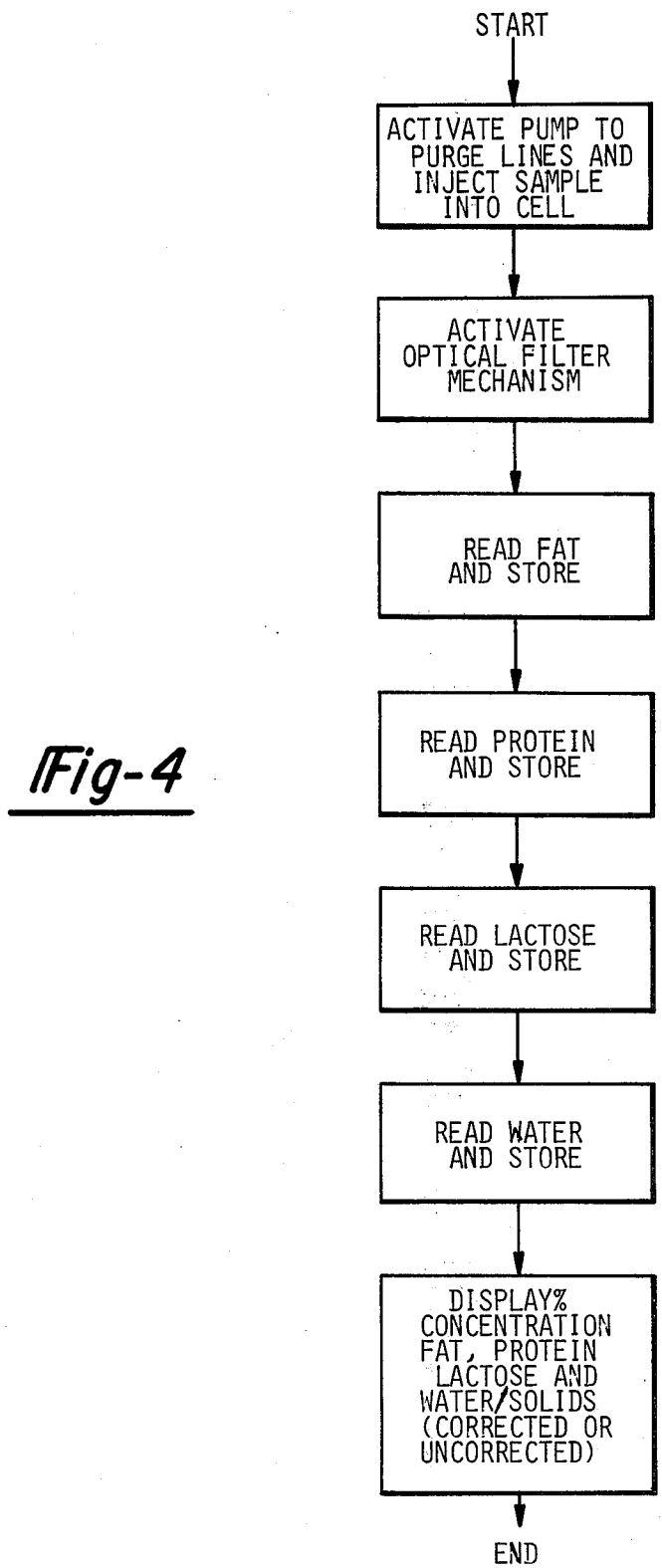
FIG. 4 is a flow chart illustrating operation of the invention.
Figure 10:
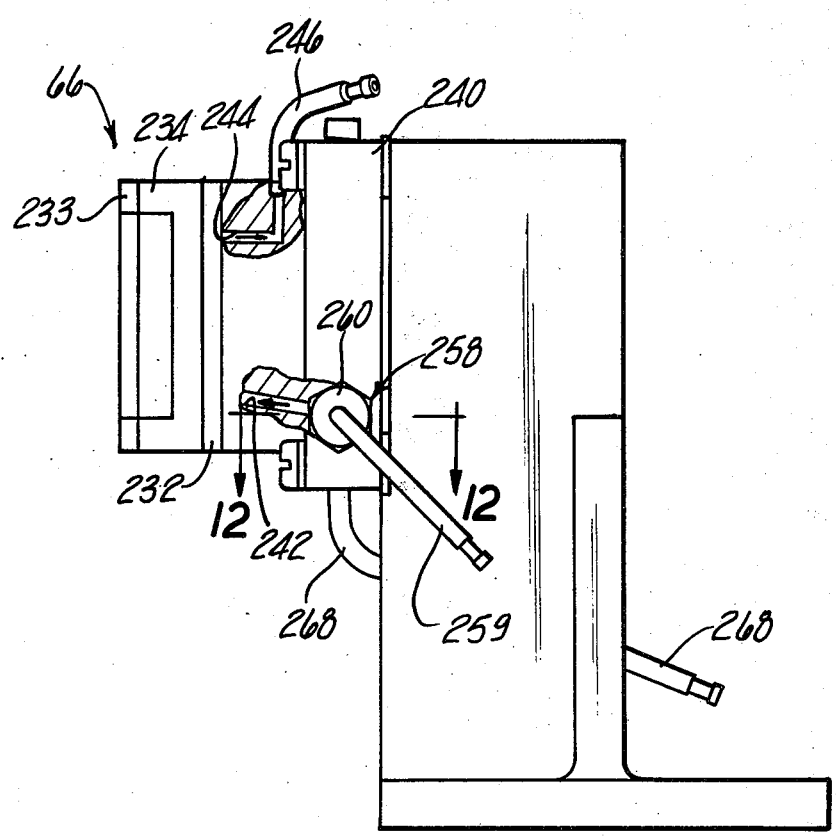
Figure 14A:
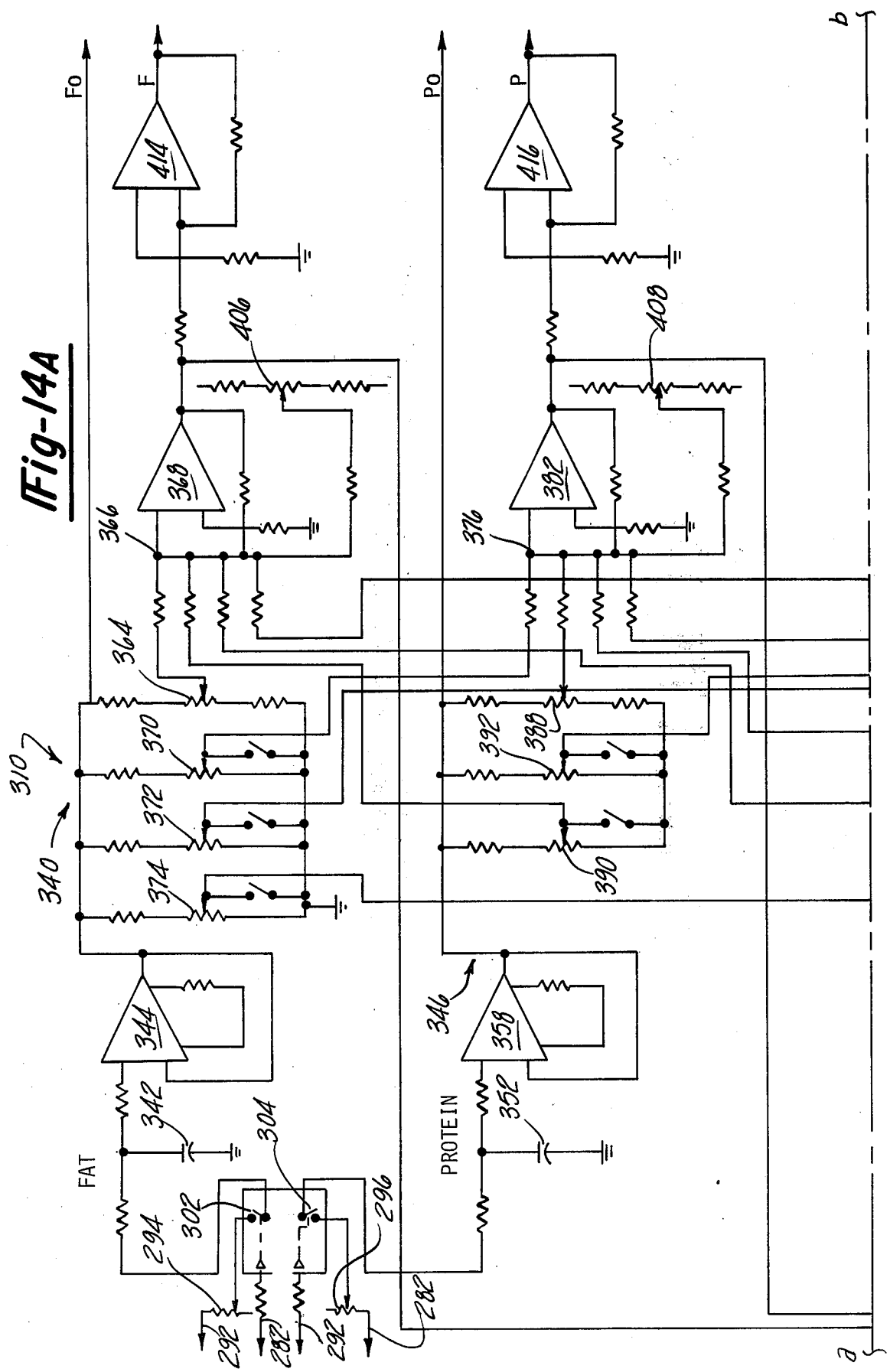
Figure 14C:
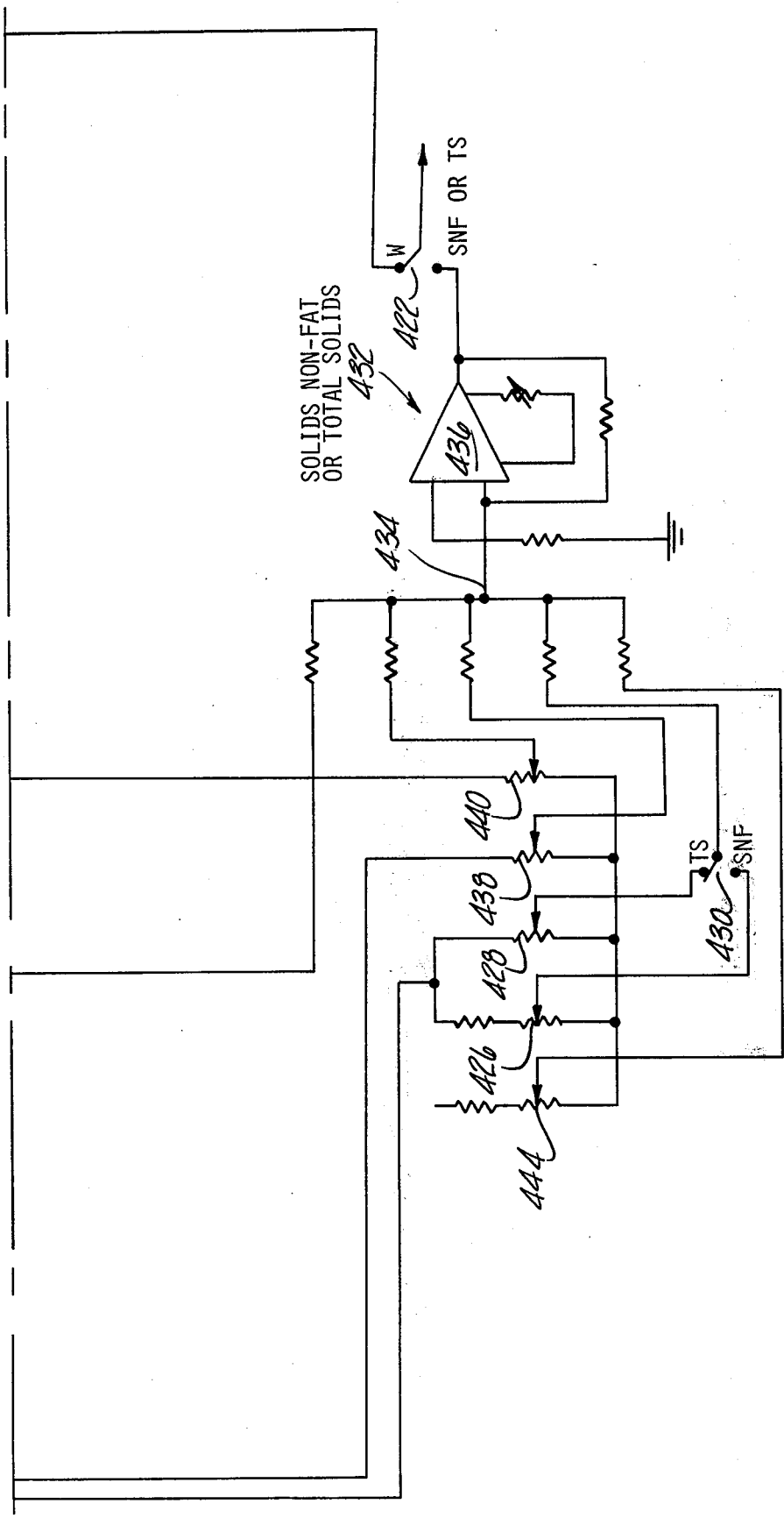

FIGS. 12 and 13 are sectional views taken along the respective lines 12—12 in FIG. 10 and 13—13 in FIG. 11; and FIGS. 14a–14c together comprise an electrical schematic diagram of the memory, correction and scaling circuitry illustrated in block form in FIG. 3, FIGS. 14a and 14b being interconnected along the lines a-b in each figure and FIGS. 14b and 14c being interconnected along the lines b-c in each figure.

The principles of invention will be described in detail in connection with a presently preferred application thereof to infrared spectrophotometric analysis of milk for percentage by weight of fat, protein, lactose and water or solids therein. However, it must be recognized that such principles are equally applicable to analysis of other dairy products, to non-dairy food products such as meat and grain, and to non-food products such as paints, pharmaceuticals or chemical and gas compositions.

Figure 1:
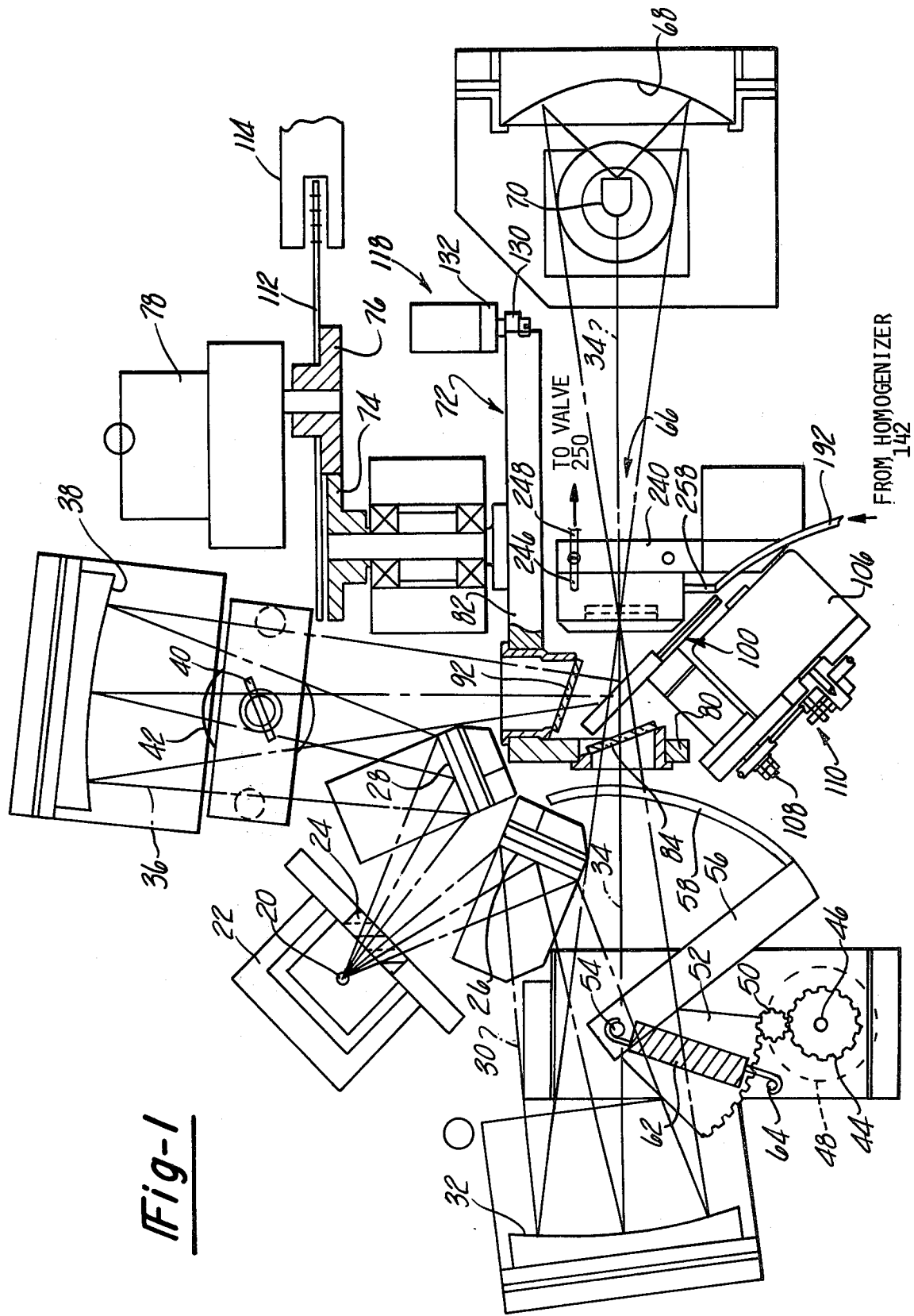
FIG. 1 is a top plan view of the optical portion of a presently preferred embodiment of the electro-optical analyzer provided in accordance with the invention.

Referring to FIG. 1, the optical section or portion of the electro-optical milk analyzer provided by the invention comprises a ceramic infrared energy source 20 enclosed within its own cooling chamber 22. An interference filter 24 having a preferred pass band in the range of three to ten microns is disposed in one wall of chamber 22 and transmits infrared energy from source 20 to a pair of plane mirrors 26,28 which operate to split the filtered infrared energy into diverging beams 30,36 illustrated in phantom lines in FIG. 1. The first or reference beam 30 is reflected by plane mirror 26 onto the surface of a spherical mirror 32 from whence reference beam 30 is focused onto an optical axis 34. The second or measurement beam 36 is reflected by plane mirror 28 onto the surface of a second spherical mirror 38 from whence the measurement beam is directed to intersect the reference beam from a direction orthogonal to beam axis 34. A sample cell generally indicated at 66 and to be described in greater detail hereinafter in connection with FIGS. 8–13 is disposed at the focus of reference beam 30 on beam axis 34. An ellipsoidal mirror 68 has a first focus at sample cell 66 and a second focus at a detector 70 for directing and concentrating the optical energy transmitted through sample cell 66 onto detector 70. Preferably, mirrors 26,28 32,38, 100 and 68 are of glass with highly reflecting surfaces of aluminum or gold.

An upstanding vane or shutter 40 is disposed in the path of measurement or reference beam 36 or 30 (drawing shows vane in measurement beam), and is rotatably coupled to a motor 42 for a purpose to be described hereinafter. A drive gear 44 is coupled to the shaft 46 of a servomotor 48 through a slipping clutch mechanism (FIG. 1 and schematically in FIG. 3) and through the idler gear 50 to a gear section 52 mounted to pivot in the plane of FIG. 1 about the pin 54. An arm 56 is rigidly coupled to gear section 52 and has a comb or shutter 58 (FIGS. 1 and 3) carried on the pivot-remote end thereof for adjustable placement within the path of reference beam 30 between mirror 32 and sample cell 66 as controlled by servomotor 48. Comb 58 is arcuate in cross section with a radius centered on the axis of pivot pin 54 and, as best seen in FIG. 3, possesses a plurality of transversely spaced longitudinal slots 60 each having a width which varies linearly with arcuate comb length. Thus, reference beam 30 is selectively attenuated as a linear function of the degree or extent to which comb 58 is inserted into the beam. Comb 58 is preferably coated with material which absorbs infrared energy. A coil spring 62 (FIG. 1) extends between arm 56 and a fixed stanchion 64 for resiliently biasing gear drive chain or transmission 44,50,52 so as to achieve substantially zero backlash. Coupled to gear 50 is an accurately linear potentiometer (schematically at 290 in FIG. 3) arranged to provide a voltage to measuring circuits which is proportional to the percentage transmission (%T) of the sample. A second potentiometer (schematically at 468 in FIG. 3) coupled to the same spindle within the same potentiometer housing provides velocity feedback for the servomotor drive circuit.

Figure 5:
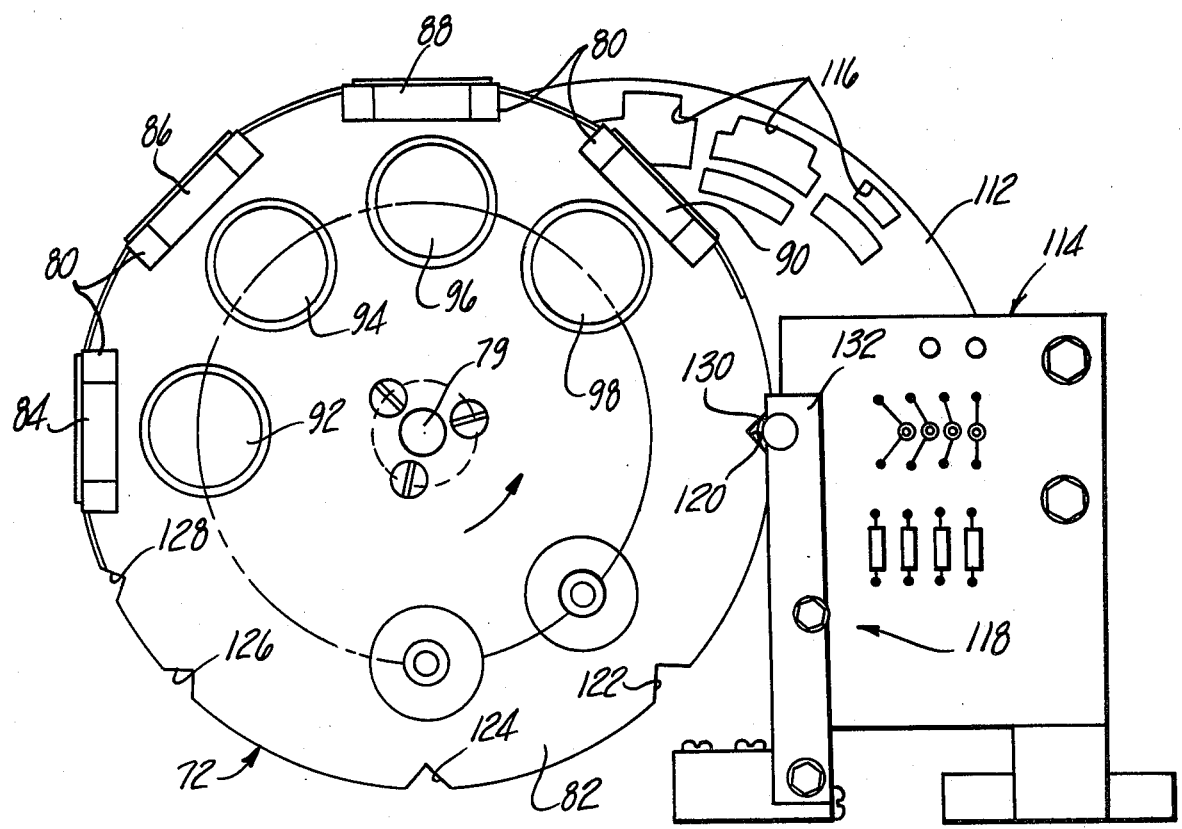
FIG. 5 is a side elevational view of the optical filter drum and coding disc assembly illustrated in FIG. 1.

A filter wheel 72 shown in FIGS. 1 and 5 comprises a drum coupled by the gears 74,76 to a drive motor 78 to rotate about a fixed axis 79 (FIG. 5) orthogonal to reference beam axis 34. Drum 72 includes segmented circumferential rim portions 80 which intersect reference beam 30 between comb 58 and cell 66 as drum 72 is rotated, and an axially facing disc portion 82 which intersects measurement beam 36. First and second series of optical absorption-type filters are respectively disposed in rim portion 80 and disc portion 82 of drum 72, and are grouped in coordinated pairs on corresponding radii from the axis of rotation 79 such that one filter in each filter pair simultaneously intersects associated ones of the reference and measurement beams 30,36. More particularly, four circumferentially spaced reference filters 84,86,88,90 are mounted in associated segments of drum rim portion 80 sequentially to intersect reference beam 30 as drum 72 is rotated in the counterclockwise direction as viewed in FIG. 5. In analysis for fat, protein, lactose and water concentrations in milk, reference filters 84–90 preferably possess nominal peak transmission wavelengths of 3.47, 6.68, 7.67 and 5.55 microns respectively. A series of circumferentially spaced measurement filters 92,94,96 and 98 are disposed on the planar disc portion 82 of drum 72 in radially aligned association with respective reference filters 84,86,88 and 90 as best seen in FIG. 5. For analysis of fat, protein, lactose and water in milk, filters 92,94,96 and 98 preferably possess nominal peak transmission wavelengths of 3.418, 6.46, 9.6 and 4.7 microns respectively. Preferably, at least fat measurement filter 84 is tiltably mounted (by means not shown) so as to facilitate factory fine-tuning of the peak transmission wavelength to the values indicated.

A detent locking arrangement 118 is provided for holding drum 72 in fixed rotational position with a filter pair in the associated beam paths. Detent 118 comprises a series of five V-shaped notches 120,122,124, 126 and 128 (FIG. 5) disposed about the periphery of drum disc portion 82. Notches 120,122,124 and 126 are respectively diametrically opposed to filter pairs 84,92; 86,94;88,96; and 90,98. Notch 128 is for holding drum 72 in a rest position. A roller bearing 130 is rotatably mounted in the plane of a drum axis 79 on a spring-biased pivot arm 132 for resiliently engaging the respective detents as drum 72 is rotated. Thus, in the position illustrated in FIG. 5, bearing 130 resiliently engages notch 120 to hold fat reference and measurement filters 84,92 in reference and measurement beams 30,36 (FIG. 1). When drum 72 is rotated to the next position wherein bearing 130 engages notch 122, protein reference and measurement filters 86,94 are held in the beam paths. Notch 124 operates in conjunction with lactose reference and measurement filters 88,96, and notch 126 operates in conjunction with water reference and measurement filters 90,98 in a similar manner.

A program or code disc 112 (FIGS. 1 and 5) is mounted on gear 76 and is thereby rotatably coupled to filter drum 72 such that a peripheral portion of disc 112 passes through the optical sensor generally indicated at 114 in FIG. 1 as a function of drum rotation. Optical sensor 114 is responsive to peripheral apertures 116 (FIG. 5 and schematically in FIG. 3) in disc 112 for controlling system electronics (FIG. 3) to stop rotation of drum 72 when a selected filter pair is disposed in the corresponding beams, to control the electronics for measurement of the particular constituent with which the filter pair is associated and to switch the pump motor on at the correct point in the operation cycle. Provision of interference filter 24 adjacent infrared source 20 (FIG. 1) for passing only a portion (three to ten microns) of the infrared spectrum of interest to the absorption-type reference and measurement filters reduces heating of the latter and improves accuracy of the overall apparatus.

Figure 6:
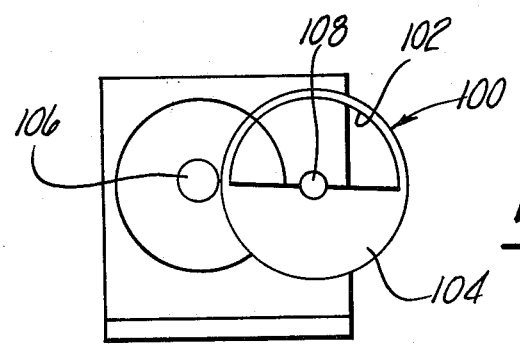
FIG. 6 is a side elevational view of the chopper disc and drive motor illustrated in FIG. 1.

A chopper shutter or disc 100 (FIGS. 1 and 6) is positioned at the zone of intersection between reference beam 30 and measurement beam 36 at an orientation of 45° with respect to both beam axes. As best seen in FIG. 1, disc 100 is angled to nest within the angle formed by drum rim and disc portions 80,82. Disc 100 comprises a semicircular aperture 102 (FIG. 6) and a semicircular reflective portion 104 alternately positioned in the paths of beams 30,36 at the point of intersection therebetween as disc 100 is rotated by the motor 106 coupled to the disc drive shaft 108 by the belt and pulley arrangement generally indicated at 110 in FIG. 1. Thus, disc 100 nested within the rim and disc portions of drum 72 is operative alternately to direct the measurement and reference beams through sample cell 66 onto detector 70. More specifically, when aperture 102 of disc 100 intersects the optical beams, reference beam 30 is transmitted on beam axis 34 through aperture 102 and sample cell 66 to detector 70 while measurement beam 36 passes through the aperture away from the sample cell. When reflective disc portion 104 intersects the respective beams, measurement beam 36 is folded thereby to focus at sample cell 66 confocally with reference beam 30, and thus is transmitted to detector 70 by ellipsoidal mirror 68. At the same time, reference beam 30 is reflected by the rear surface of disc portion 104 away from the sample cell.

Thus, rotation of disc 100 at the preferred frequency of 12.5 hertz (50 hertz mains frequency) or 15 hertz (60 hertz mains frequency) operates to transmit to detector 70 a composite beam which alternates in intensity as a function of the difference in percentage transmission of a sample in cell 66 at the particular wavelengths transmitted by whichever reference and measurement filters are in the beam paths. Detector 70 produces a signal which is amplified and conditioned by amplifier 111 and associated circuitry (FIG. 3) to drive servomotor 48 (FIGS. 1 and 3). This positions comb 58 within beam 30 so as to minimize this intensity differential. In this manner, the ultimate position of the servomotor 48, and the potentiometer coupled to it, for any filter pair, is proportional to the change in transmission of the sample situated in cell 66 at the wavelengths transmitted by that filter pair.

Figure 2:
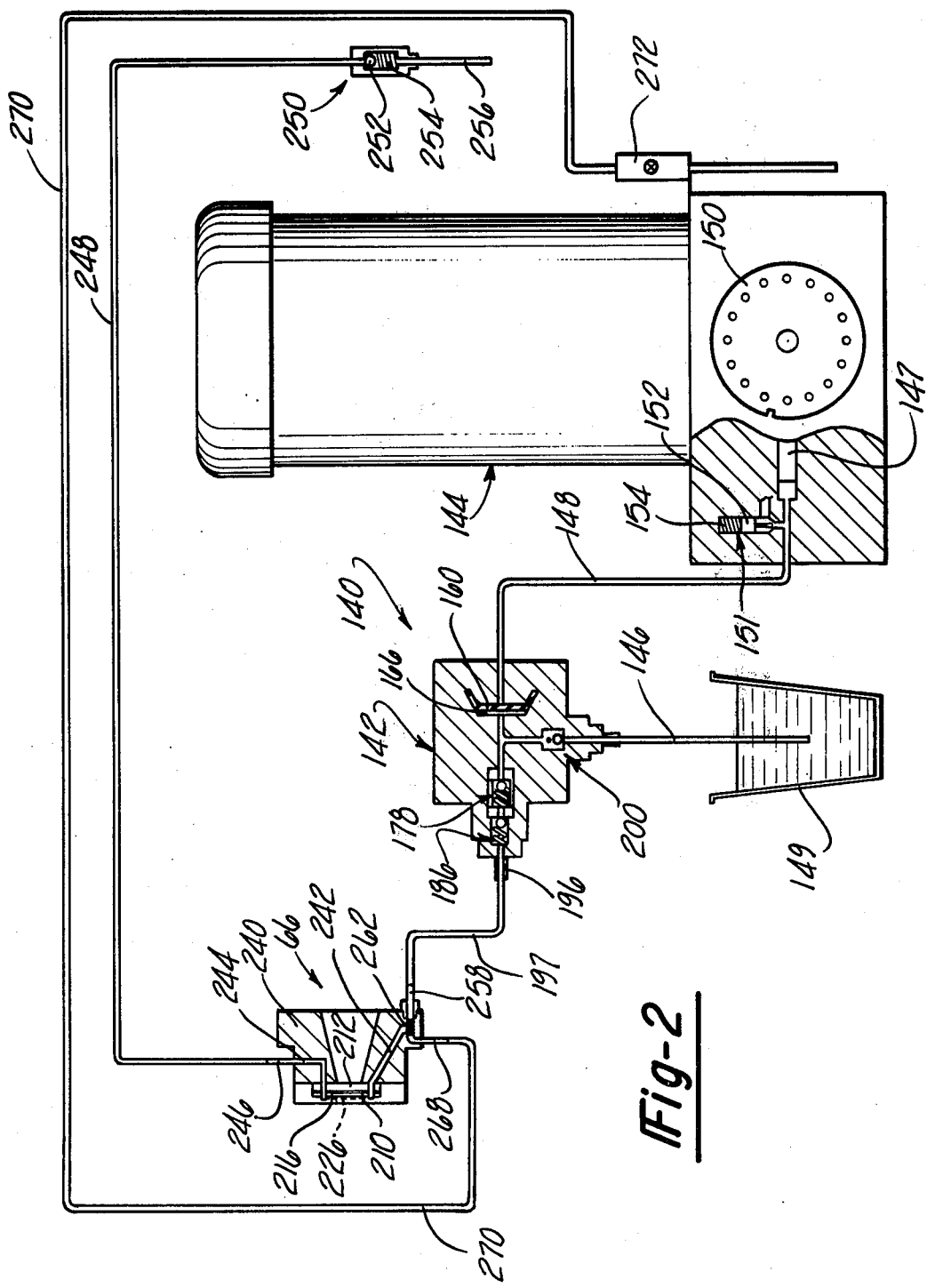
FIG. 2 is a schematic diagram of a system for directing fluid to be analyzed to the sample cell in accordance with the presently preferred embodiment of the invention.

FIG. 2 illustrates a presently preferred embodiment 140 of the fluid drive system for placing test fluid in the sample cell generally indicated at 66 in FIG. 1. System 140 comprises a diaphragm-type homogenizer 142 (FIGS. 2 and 7) operatively coupled to an hydraulic pump 144 (FIG. 2) and having an inlet 146 to draw a fluid milk sample from the vessel 149. Pump 144 includes a reciprocable piston 147 for driving hydraulic fluid under pressure to homogenizer 142 through the conduit 148. A code disc illustrated schematically at 150 in FIG. 2 is coupled to the piston drive mechanism (not shown) for cyclically operating pump 144 in a manner to be described. A pressure relief valve 151, including a valve stem 152 and a coil spring 154, is coupled internally of pump 144 to conduit 148. In one working embodiment of the invention, pump 144 comprises a Series (1) Actuator Pump marketed by Dia-meter Pumps Ltd.

of Unit 6, Fort Fareham Industrial Estate, Fareham, Hampshire, PO14 1AH.

Figure 7:
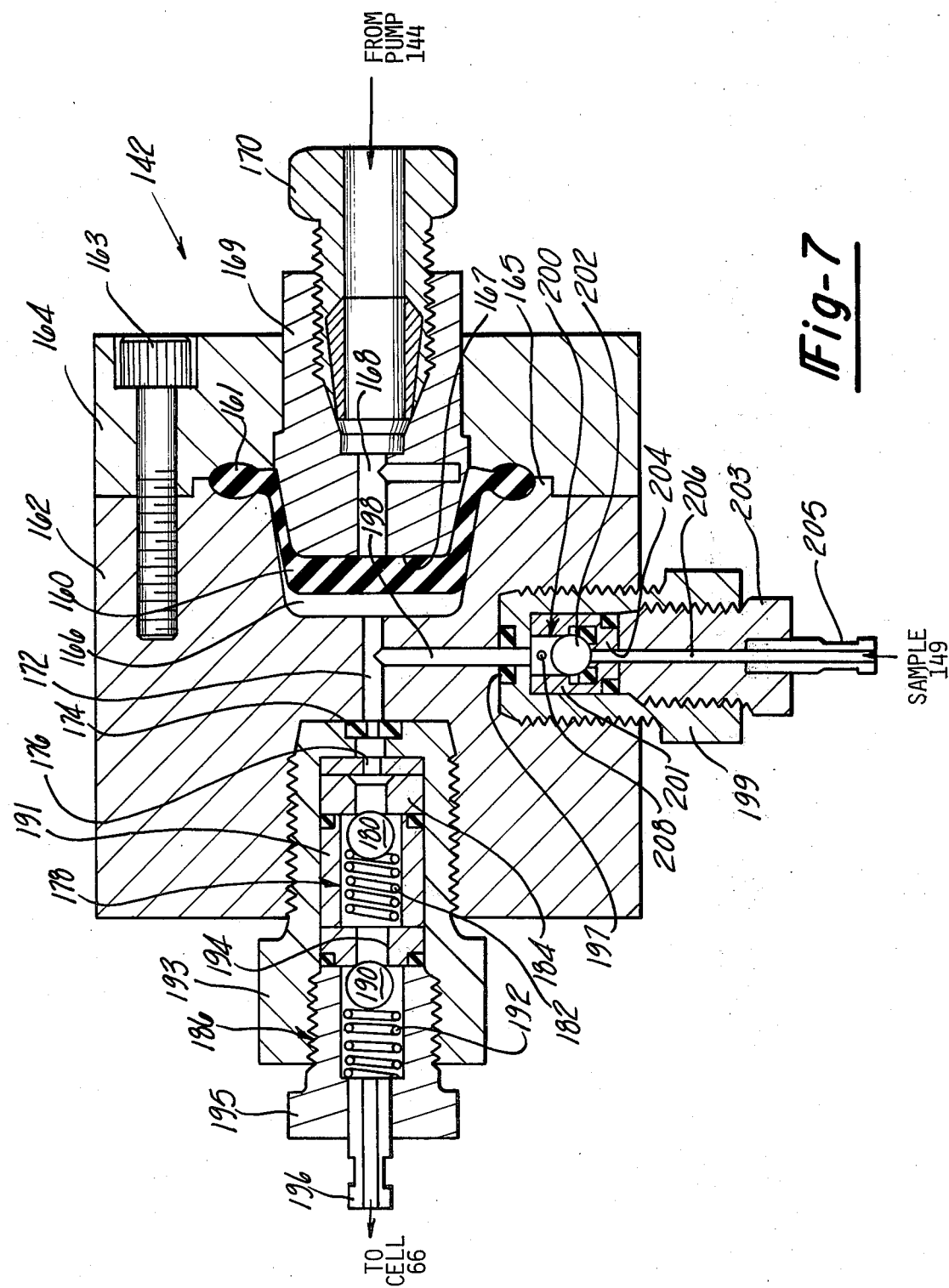
FIG. 7 is a sectional view of the homogenizer in accordance with the invention and illustrated schematically in FIG. 2.

Referring to FIGS. 2 and 7, homogenizer 142 includes a resilient diaphragm 160 having an annular lip 161 captured between body blocks 162,164. The central portion of diaphragm 160 is disposed within a diaphragm pump chamber 166. On one side of diaphragm 160, chamber 166 is coupled by passage 168 extending axially through a fitting 169 to a nipple 170 threadably received in fitting 169 for receiving hydraulic pump fluid through conduit 148 (FIG. 2). The other end 167 of fitting 169 acts as a diaphragm stop on the decompression stroke of the pump cycle. Fitting 169 is rigidly attached to block 164 and lip 171 takes the axial load imparted on the compression stroke. An annular lip 165 in block 162 insures accurate location of the diaphragm stop 167 in relation to the diaphragm 160. High tensile bolts 163 are used to fasten together blocks 162,164. A second passage 172 extends axially in block 162 from chamber 166 through a gasket 174 and an orifice 176 to a first homogenizing valve generally indicated at 178.

Valve 178 comprises a sapphire ball 180 normally biased by a coil spring 182 against a ceramic valve seat 184 restricting fluid communication from diaphragm chamber 166. Valve 178 opens to a second homogenizing valve 186 comprising a sapphire ball 190 biased by a coil spring 192 against a stainless steel valve seat 194. Valve 186 opens to a nipple 196. Nipple 196 is cemented into a fitting 195 which encloses spring 192 and ball 190, and which in turn is threadably received into a larger fitting 193. Fitting 193 encloses orifice 176 and valve seats 184,194, all of which are held rigidly therein under compression by fitting 195 in cooperation with a sleeve 191 surrounding ball 180 and spring 182. Fitting 193 is threadably received in block 162 and captures gasket 174 in sealing engagement around the diaphragm-remote end of passage 172.

A passage 198 extends laterally of passage 172 to a gravity and pressure operated check valve 200 comprising a ball 202 normally biased by gravity downwardly against a valve seat 204. A passage 206 extends from valve seat 204 to a nipple 205 for receiving a fluid sample through conduit 146 (FIG. 2). Nipple 205 is cemented into a fitting 203 which, in turn, captures valve seat 204, ball 202 and a ball-guide sleeve 201 within an outer fitting 199 by being threadably received in the latter. Fitting 199 is threadably received within block 162 in axial alignment with lateral passage 198 and captures a sealing gasket 197 therearound. Upward motion of ball 202 during suction of diaphragm 160 is limited by a pin 208 press fitted in and extending across sleeve 201.

Orifice 176 passes through a removable disc of stainless steel and is included in the homogenizer head merely as a means of enabling the parts to be disassembled. The valve seats, balls and springs may be removed from the separated homogenizer unit by first unscrewing fitting 195 from fitting 193, and then pressing a rod against the disc containing the smaller orifice 176 in a direction from right to left as shown in FIG. 7.

In operation, pump 144 alternates between a negative or suction pressure with reference to homogenizer 142 wherein diaphragm 160 is withdrawn to the position illustrated in FIGS. 2 and 7, and fluid to be homogenized and tested is drawn by negative pressure through conduit 146 and check valve 200 (FIG. 7) into chamber 166. On the next succeeding pressurization stroke, the diaphragm 160 is displaced to the left in FIGS. 2 and 7 forcing the sample fluid drawn during the suction portion of the pump cycle through orifice 176 and valves 178,186 to outlet nipple 196. Preferably, the stroke of piston 147 (FIG. 2) is slightly greater than the volume of diaphragm chamber 166 such that pressure relief valve 151 (FIG. 2) is actuated on each stroke for deaerating the pump hydraulic fluid. Valve 151 preferably is set at 3800 psi. In the homogenizer illustrated in FIGS. 2 and 7, a pump pressure in the range of 3000 to 5000 pounds per square inch, typically 3500 psi, is contemplated. High pressure operation in this range and the two-stage homogenizing valve arrangement 178,186, has been found to reduce the particle size of the larger globules in whole milk to about two microns.

Figure 8:
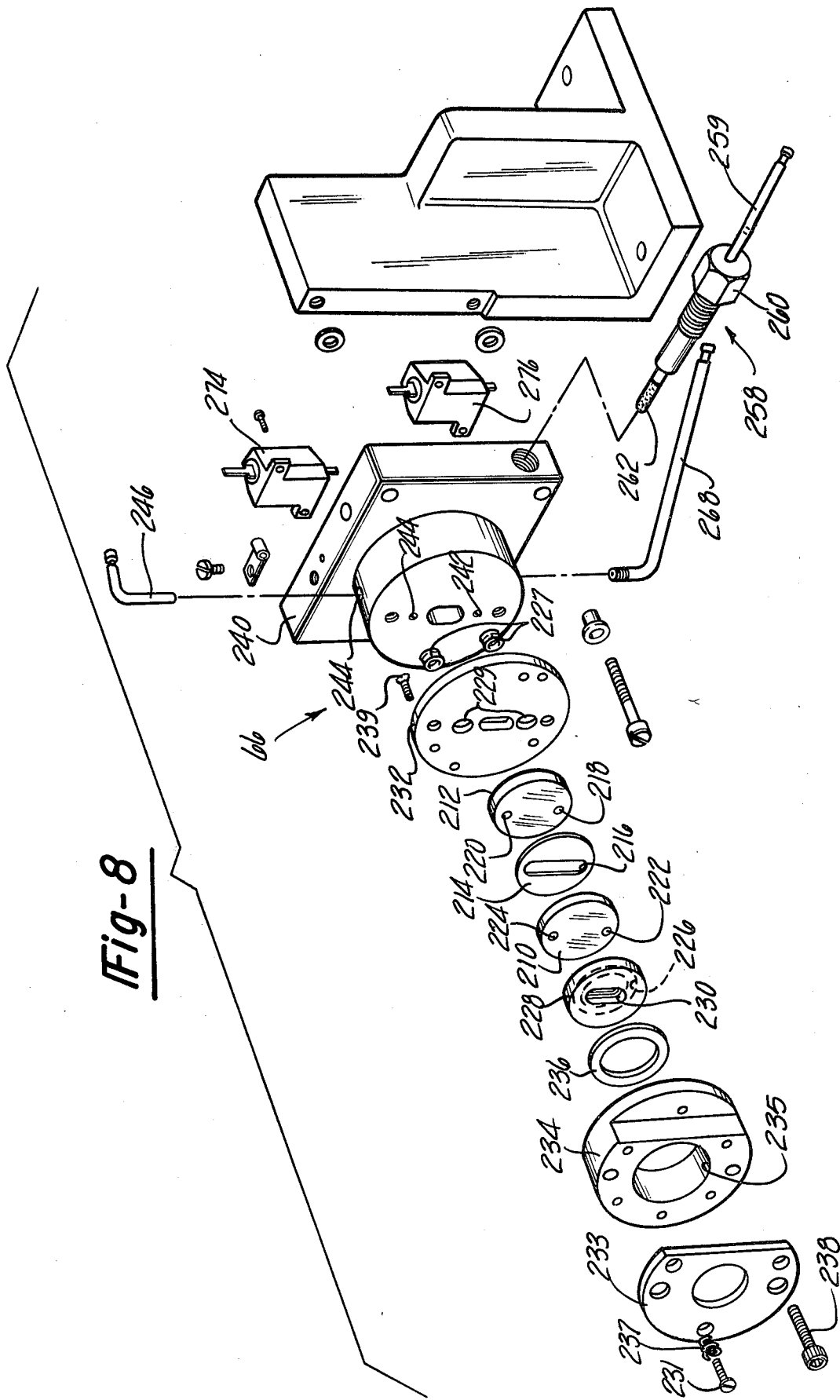
FIG. 8 is an exploded perspective view of a presently preferred embodiment of the sample cell in accordance with the invention.

Sample cell 66 is illustrated schematically in FIG. 2 and in greater detail in FIGS. 8-13. Cell 66 comprises a pair of flat parallel optical windows 210,212 spaced from each other in assembly by a shim 214 of controlled thickness and having an oval center opening for providing a planar sample zone 216 between windows 210,212. In the preferred embodiment of the invention for measuring fat, protein, lactose and water concentrations in milk, shim 214 and, therefore, planar sample zone 216 possess a thickness of thirty-seven microns. One of the windows 210,212 is constructed of calcium fluoride material having a cut-off at approximately 11 microns while the other window is of barium fluoride material having a cut-off at 12.5 to 13 microns. As best seen in FIGS. 8 and 13, window 212 has a pair of circular openings 218,220 extending therethrough transversely of oval sample zone 216 and spaced from each other lengthwise of the sample zone such that fluid entering opening 218, which is an inlet opening, traverses the sample zone in the upward direction in FIG. 13 and then exists opening 220, which is the outlet opening. Second openings 222,224 extend through outer window 210 in respective alignment with inlet opening 218 and outlet opening 220, and communicate with a circular groove or channel 226 of semicircular section having a preferred diameter of 0.3 mm formed on the face of a stainless steel plate 228 cemented to window 210, such that a portion of the fluid entering inlet 218 will flow through opening 222, channel 226, opening 224 and then exit outlet 220 thereby to bypass sample zone 216. Plate 228 has an oval center opening 230 for admitting infrared radiation therethrough to windows 210,212.

Windows 210,212, shim 214 and plate 228 are placed in facing engagement as described. As best appreciated with reference to FIGS. 8 and 13, this sandwiched assembly is then located together with a centrally apertured ring 236 within the machined central bore 235 of a cylindrical block 234. A pair of plates 232,233 having central openings of smaller aperture than bore 235 are then placed over the axial faces of cell block 234 and fastened thereto by the pan head screws 231 and flat head screws 239 to hold the sandwiched assembly within the cell block. Holes in 233 are counterbored to take springs 237 under the heads of screws 231. Springs 237 serve to spring-load parts 236, 228, 210, 214 and 212 together between plates 233 and 232 to give equal surface loading on all parts. Holes in plate 233 are large enough to allow heads of screws 238 to pass therethrough and bed against the surface of block 234. Plate 232 has openings 229 which align with openings 218,220 in window 212 and which receive sealing rings 227. The entire cell block assembly is then fastened to a port block 240 by the screws 238.

Figure 9:
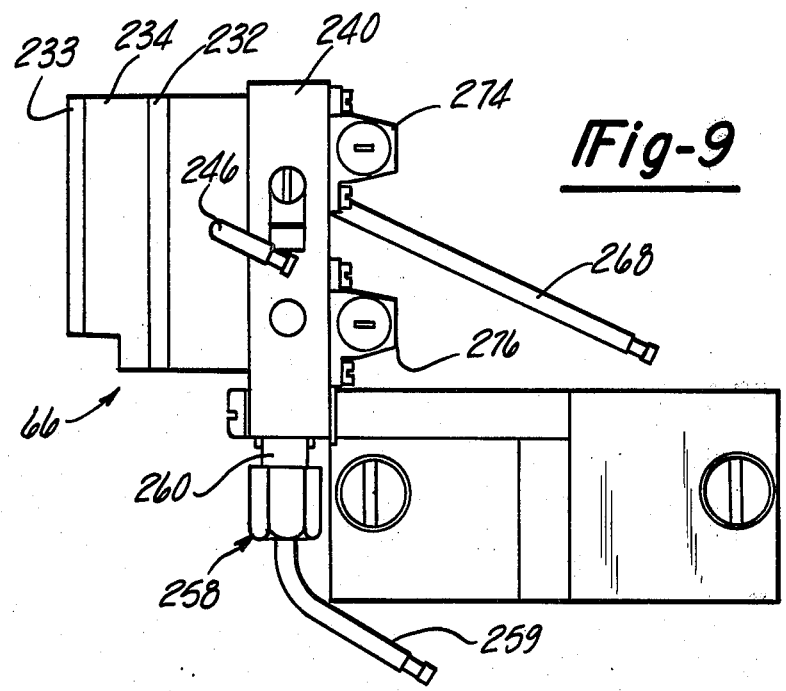

Port block 240 includes inlet and outlet passages 242,244 (FIGS. 8, 10, 12 and 13) respectively communicating with openings 218,220 in window 212 through plate openings 229. Outlet passage 244 in block 240 communicates through a tubular nipple 246 (FIGS. 9-11) and a conduit 248 (FIG. 2) with a pressure valve 250 comprising a ball 252 biased by coil spring 254 to retard flow through conduit 248 (and therefore through cell 66). Valve 250, when opened, feeds fluid in conduit 248 to waste through a drain 256. An inlet assembly 258 (FIGS. 9-12) comprises a fitting 260 threadably received into a side opening in block 240 and a hollow tubular filter 262 extending axially from fitting 260 into a cylindrical flow passage 264 in block 240. A passage 266 (FIGS. 11 and 12) communicates transversely with passage 264 axially spaced from filter 262, and extends through block 240 to a second outlet nipple 268 (FIGS. 9-11). Outlet nipple 268 is connected by a conduit 270 (FIG. 2) to a valve 272 controlled by disc 150 in pump 144. Nipples 246,268 are screwed and cemented into associated openings in port block 240. As best seen in FIG. 12, inlet passage 242 in block 240 communicates with passage 264 at right angles approximately centrally of filter 262 such that fluid entering passage 242 passes through the filter side wall and is filtered thereby. A nipple 259 is a running fit into fitting 260 for connection to conduit 197 (FIG. 2) from homogenizer 142.

Thus, it will be evident that, with pressure valve 250 (FIG. 2) normally closed and control valve 272 held normally open, fluid fed to sample cell inlet 258 by homogenizer 142 normally flows through the hollow central opening in filter 262, through passages 264,266, nipple 268 (FIGS. 11 and 12), conduit 270 (FIG. 2) and valve 272 to waste, whereby filter 262 is self-cleaning. On the other hand, when valve 272 is closed, fluid pulses from homogenizer 142 are routed through the side wall of filter 262 into passage 242 (FIGS. 2, 10 and 12-13) in block 240. A portion of this fluid passes through sample zone 216 while the remainder bypasses the sample space through channel 226 (FIG. 13) in plate 228 as previously described. Disc 150 (FIG. 2) controls pump 144 such that each sampling cycle comprises a plurality of between five and fifteen, preferably twelve, pulsations of homogenizer 142. On the first eleven pulsations in the preferred mode of operation, valve 272 is held open such that the homogenized milk effectively purges homogenizer 142, conduit 197 and inlet assembly 258. In particular, it will be appreciated that the purging fluid tends to wash tubular filter 262. Prior to the twelfth pulsation of homogenizer 142, valve 272 (FIG. 2) is closed. Thus, the pressure of the twelfth pulsation is effective to open pressure valve 250 such that fluid is then routed through the side wall of tubular filter 262 and through sample zone 216 as previously described. After the twelfth pulsation, operation of pump 144 is automatically terminated by disc 150 (FIG. 2) and optical characteristics of the sample in sample zone 216 may be measured.

Preferably, each pulsation of homogenizer 242 provides approximately 0.6 milliliters of homogenized fluid. The sample zone 216 itself holds approximately 0.005 milliliters of fluid. Thus, it will be appreciated that the total volume of fluid provided by homogenizer 142 during each purging and cell-refill cycle, and also during the twelfth pulsation through the sample zone itself, is substantially in excess of that required for obtaining a measurement sample. However, the additional wastage offers the significant advantage previously described of automatically purging all flow lines including the cell. Preferably, conduits 197,270 and 248 (FIG. 2) are constructed of resilient material such as tubular PVC for elastically absorbing transient pressures caused by the pulsating fluid flow thereby to prevent flexure of optical windows 210,212.

Plates 228, 233, 232, cell block 234, ring 236 and port block 240 (FIG. 8) are preferably constructed of corrosion resistant material such as stainless steel. Heating resistors 274,276 are mounted on the cell-remote side of block 240 and are connected to appropriate control circuits 278 (FIG. 3) for heating block 240 and thereby maintaining the temperature of sample cell assembly 66 at a selected temperature above instrument temperature. For analysis of milk, a cell temperature of $40° \pm 0.2°$ C. is preferred. Temperature control circuit 278 may comprise a suitable bridge circuit or the like responsive to a thermistor 280 (FIGS. 3 and 11) mounted on the port block assembly 240. Similar temperature control structure is preferred in connection with homogenizer 142 but is not illustrated in FIG. 7. Preferably, homogenizer 142 is physically located closely adjacent to cell 66 but external to the optics unit, and test measurements are performed a short time after fluid sample is placed in the cell so that the homogenized fat particles in the milk do not have an opportunity to form aggregates.

Instrument measuring and control circuits are illustrated in functional block form in FIG. 3 and include decoding circuitry 282 responsive to coded apertures 116 in program disc 112 through optical sensor 114 for indicating which of the filter pair on drum 72 is in the beam paths, and thereby controlling the remainder of the circuits for measurement of fat, protein, lactose and water/solids concentrations. Detector 70 is connected through the normally closed contacts of a run/calibrate switch 284 to the input of amplifier 111, which is a.c. coupled and tuned to $12.5 \pm 3$ Hz (for 50 hertz line frequency) or to $15 \pm 3$ Hz (for 60 hertz line frequency). Connection of detector 70 to amplifier 111 is through one of four variable resistors 450-456 (selected through switches 460-466 by photoposition decoding circuitry 282 for fat, protein, lactose and water/solids respectively) which determines the servo amplifier voltage gain and hence sensitivity to the detector signal voltage for each component being measured. The amplifier output drives servomotor 48 which controls the comb position.

A voltage derived from the potentiometer 468 coupled to the comb mechanism provides velocity feedback to amplifier 111 insuring a controlled rate of comb movement. Also coupled to the comb mechanism is the precision potentiometer 290. Thus, a voltage directly proportional to comb position is provided to an input of amplifier 470. Summed to this amplifier is a voltage derived from one of four preset adjustable resistors 472-478 selected through switches 480-486 by photoposition decoding circuitry 282 for fat, protein, lactose and water/solids respectively. This provides a bias to the comb position voltage prior to logging by log amplifier 292. Adjustment of the bias allows the output of the log amplifier 292 to be linear for equal increments of %T of the component being measured in the cell in accordance with Beer's law. Beer's law is: $D = \ln 1/T$ for D equals optical density, T equals percent transmission and ln indicates the taking of the natural logarithm (base e).

The sequential concentration signals from log amplifier 292 are fed by slope control resistors 294-300 through switches 302-308 controlled by disc decode circuitry 282 to a four-channel memory, correction and scaling circuit 310 which will be described in greater detail in connection with FIG. 14. Circuit 310 provides at its output a series of uncorrected signals $F_o, P_o, L_o$ and $W_o$ for fat, protein, lactose and water respectively, and a second series of signals F, P, L and W/S which have been cross-corrected for effects due to change in absorption of infrared energy at the particular test wavelengths selected for the others. The outputs of circuit 310 are connected through a four-pole double-throw switch generally indicated at 312 for selecting either corrected or uncorrected signals, and through a four-channel a/d converter 314 to digital readouts 316, 318, 320 and 322 for indicating concentration in percentage by weight of fat, protein, lactose and water or solids respectively. Displays 316–322 preferably comprise decimal displays.

The decoded outputs of circuit 282 are additionally connected to an optical zero adjustment circuit 324 which controls the position of vane 40 (FIG. 1) by means of motor 42. Zero adjust circuit 324 receives second control inputs from the manually adjustable resistors 326, 328, 330 and 332 for placing vane 40 (FIG. 1) in the desired zero adjustment position for fat, protein, lactose and water respectively. Calibration of zero adjustment circuit 324 and of memory, correction and scaling circuit 310 will be discussed in greater detail hereinafter. It will be appreciated, of course, that the various resistors illustrated in FIG. 3 (and in FIG. 14 yet to be described) are to be connected to appropriate biasing voltages such as +12 volts, −12 volts and zero volts.

Referring now to FIGS. 14a–14c, memory correction and scaling circuitry 310 illustrated therein basically comprises four circuit channels 340, 346, 348 and 350 (FIGS. 14a–14b) respectively labeled for providing corrected and uncorrected indications of fat, protein, lactose and water concentrations, and a fifth channel 432 (FIG. 14c) for deriving an indication of non-fat solid concentration or total solid concentration from signals available in the other four channels. Fat channel 340 receives an input signal from adjustable scaling resistor 294 (FIGS. 3 and 14a) through switch 302, which preferably comprises an FET switch controlled by disc decode electronics 282 as previously described. The switched input signal is fed and stored on a capacitor 342 across the input of a high impedance input current amplifier 344 which provides at its output the uncalibrated fat signal $F_o$. Similarly, protein, lactose and water channels 346, 348 and 350 each include a corresponding storage capacitor 352, 354 and 356 connected across the input of the high impedance input amplifiers 358, 360 and 362 for providing uncorrected protein, lactose and water signals $P_o, L_o$ and $W_o$ respectively.

The output of fat input amplifier 344 is connected in fat channel 340 through an adjustable resistor 364 to a summing junction 366 at the input of second stage amplifier 368. The output of amplifier 344 is also connected through the adjustable resistors 370 and 372 to the summing junctions 376 and 378 at the inputs of second stage amplifiers 382 and 384 in protein and lactose channels 346 and 348, and through the adjustable resistor 374 to one input of the second stage amplifier 386 in water channel 350. The output of protein input amplifier 358 is connected through an adjustable resistor 388 to protein summing junction 376, through a second adjustable resistor 390 to fat summing junction 366, and through a third adjustable resistor 391 to lactose summing junction 378. The output of lactose input amplifier 360 is connected through a first adjustable resistor 394 to lactose summing junction 378, through a second adjustable resistor 396 to protein summing junction 376, and through a third adjustable resistor 398 to fat summing junction 366. The output of water input amplifier 362 is fed to a summing junction 380 at a second input of second stage amplifier 386, the output of which is connected to fat summing junction 366 through the adjustable resistor 400, to protein summing junction 376 through adjustable resistor 402 and to lactose summing junction 378 through the adjustable resistor 404. Summing junctions 366, 376, 378 and 380 are additionally connected to the adjustable resistors 406, 408, 410 and 412 respectively.

Second stage amplifier 368 in fat channel 340 is connected through an output amplifier 414 for providing an analog signal (voltage) F as a linear function of fat concentration and corrected for cross-absorption effects as previously described. Similarly, protein and lactose second stage amplifiers 382 and 384 are connected through corresponding output amplifiers 416 and 418 for providing corrected analog protein and lactose signal (voltages) P and L. The output of amplifier 386 in water channel 350 is connected through an output amplifier 420 to one selectable contact of a switch 422 which selects either water concentration W or one of the solid concentrations TS (total solids) or SNF (solids non-fat) for display on digital readout 322 (FIG. 3). The output of second stage amplifier 368 in fat channel 340 is additionally connected to solid channel 432 through the adjustable resistors 426 and 428 to the two selectable contacts of a switch 430 for choosing TS or SNF for display. The common contact of switch 430 is connected to a summing junction 434 at the input of an amplifier 436. The output of second stage amplifier 382 in protein channel 346 is connected through an adjustable resistor 438 to solid summing junction 434. The output of lactose second stage amplifier 384 is connected through the adjustable resistor 440 to junction 434, and the output of water second stage amplifier 386 is connected through an adjustable resistor 442 (FIG. 14b) to summing junction 434. An adjustable resistor 444 provides an offset voltage to compensate in the solids and solids non-fat readout for the average value of mineral matter in milk. The wipers of adjustable resistors 370, 372 and 374 in fat channel 340, 390 and 392 in protein channel 346, 396 and 398 in lactose channel 348, and 400, 402, 442 and 404 in water channel 350 have normally open switches connected thereacross to ground for short circuiting the respective adjustable resistors during the calibration operation to be described.

Corrected signals for fat F, protein P, lactose L, water W, total solids TS and solids non-fat SNF are given by the following equations:

$F = aF_o + bP_o + cL_o + dW + e$ $P = fF_o + gP_o + hL_o + iW + j$ $L = kF_o + mP_o + nL_o + oW + p$ $W = W_o + qF_o + r$ $TS = sF + tP + uL + xW + v$ $SNF = wF + tP + uL + xW + v$ wherein the coefficients a-x are predetermined empirically and are adjusted by the variable resistors in FIGS. 14a–14c.

| coefficient | calibrated by variable resistor |
| --- | --- |
| a | 364 |
| b | 390 |
| c | 398 |
| d | 400 |
| e | 406 |
| f | 370 |
| g | 388 |
| h | 396 |
| i | 402 |
| j | 408 |
| k | 372 |
| m | 392 |
| n | 394 |
| o | 404 |
| p | 410 |
| q | 374 |
| r | 412 |
| s | 428 |
| t | 438 |
| u | 440 |
| v | 444 |
| w | 426 |
| x | 442 |

The values of coefficients a-x depend upon the characteristics of the filters and vary a great deal from one filter batch to another.

Before discussing overall operation of the invention, the method of calibration will be briefly described. First, referring to FIGS. 1–3, pump 144 is operated to draw water, preferably distilled water, into homogenizer 142 and pulse water through the fluid system to purge the homogenizer, the various conduits and sample cell 66. A "sample" of water is left in the sample cell. Servomotor 48 is turned on and switch 312 (FIG. 3) is in the uncorrected position. Filter drum 72 (FIG. 1) is then operated sequentially to place the fat, protein, lactose and water filter pairs in the respective optical beams. With the fat filters in the beams, for example, and chopper 100 energized such that radiation is incident on detector 70 as an alternating function of the intensity of the sample and reference beam passing through the sample cell, resistor 326 (FIG. 3) is adjusted until the arcuate comb 58 is in an arbitrary "zero" position which yields a "zero" reading at display 316. As resistor 326 is adjusted, vane 40 (FIG. 1) is correspondingly adjusted to selectively attenuate measurement beam 36 so that the measurement and reference beams at 3.418 and 3.47 micron wavelength respectively are equal in intensity at detector 70. This procedure is then repeated for protein, lactose and water successively, such that resistors 328,330 and 332 (FIG. 3) are adjusted to correspond to zero positions for each of these measurements respectively. Thereafter during measurement operations, optical zero adjust circuitry 324 (FIG. 3) will automatically rotate vane 40 by means of motor 42 to the adjusted zero position depending upon the constituent to be measured.

With switches 430 and 422 (FIG. 14c) in the TS or total solids position, servomotor 48 (FIG. 3) is disconnected (by switch means not shown) and resistor 444 (FIG. 14c) is adjusted until the reading on display 322 (FIG. 3) is equal to the sum of displays 316,318 and 320. With servo 48 off, filter drum 72 is then rotated to the fat position and resistor 294 (FIGS. 3 and 14a) is adjusted while switch 312 is sequentially switched back and forth between corrected and uncorrected positions until the corrected and uncorrected fat signals indicated at readout 316 are identical. The same procedure is then repeated for protein, lactose and water such that adjustable resistors 294–300 are in their calibrated positions.

Drum 72 is then again returned to the fat position and switch 284 (FIG. 3) is placed in the calibrate position wherein servo amplifier 286 is connected to adjustable resistor 288. Servomotor 48 is re-energized and resistor 288 is adjusted until digital display 316 reads "10.00" with switch 312 in the uncorrected position. The switches across adjustable resistors 370,372 (FIG. 14a) are open and the remaining switches across the various adjustable resistors in FIG. 14 are closed. Resistors 364,370 and 372 are then adjusted while switch 312 (FIG. 3) is alternately switched between corrected and uncorrected positions until the corrected fat signal equals 10a, i.e. $aF_o$, the corrected protein signal equals the uncorrected P signal ($P_o$) plus 10f and the corrected lactose signal equals the uncorrected signal $L_o$ plus 10k. Filter drum 72 (FIG. 1) is then moved to the protein position and resistor 288 is adjusted to yield an uncorrected signal $P_o$ on display 318 of "10.00". The switches across adjustable resistors 390,392 (FIG. 14a) are opened and the remaining resistor-bridging switches in FIG. 14 are closed. Resistors 388,390 and 392 are then adjusted while switch 312 (FIG. 3) is alternately switched between corrected and uncorrected positions until the corrected protein signal on display 318 is equal to 10g, i.e. $gP_o$, the corrected fat signal at display 316 is equal to the display at the uncorrected position of switch 312 plus 10b and the corrected lactose signal at display 320 is equal to the signal in the uncorrected position of switch 312 plus 10m. Drum 72 is then rotated to the lactose position and resistor 288 is adjusted to yield an uncorrected lactose signal at display 320 of "10.00". The switches bridging resistors 396 and 398 (FIG. 14b) are opened and the remaining resistor-bridging switches in FIG. 14 are closed. Resistors 394,396 and 398 are then adjusted while switch 312 (FIG. 3) is alternately switched between corrected and uncorrected positions until the corrected lactose signal at display 320 is equal to 10n, the corrected fat signal at display 316 is equal to the signal when switch 312 is in the uncorrected position plus 10c and the corrected protein signal at display 318 is equal to the signal when switch 312 is in the uncorrected position plus 10h. Servomotor 48 is then turned off. All resistor-bridging switches in FIG. 14 are closed and switch 312 is placed in the uncorrected position. Resistor 444 (FIG. 14c) is then re-adjusted until the display at 322 is equal to the sum of the displays at 316–320 plus the required correction constant v.

For normal application to the analysis of whole milk for fat, protein, lactose and solids or solids non-fat, circuits 340,346,348 and 432 will normally be used. Up to now it has not been found necessary to apply water corrections to the fat, protein, or lactose channels. At the time of determining the design features of the invention described herein, it was visualized that the water channel could be employed in the following ways.

(1) As an extra means of applying cross corrections to fat, protein, lactose channels and thus indirectly to solid channel for variation in mineral matter. This has not proven to be worthwhile, presumably because the mineral matter being of high specific gravity, or small bulk, displaces little water and therefore shows little sensitivity to change in content of mineral matter. The means for applying these corrections are still available and the coefficients are adjusted in the same way as described for fat, protein and lactose but using resistors 400,402,404,442.

(2) As a direct means of determining total solids or solids non-fat. This is effected by measuring at the water wavelengths the displacement of water by other components and relating this directly to results obtained from standard methods (e.g. gravimetric and hydrometer). Results compared by these two methods (instrument v. either standard) have given standard deviations of 0.1%. However, standard deviations as low as 0.07–0.08% are easily achieved using the summation method and, to date, this latter method has been preferred. Note: when this direct method is used for solids non-fat, the effect of fat is offset by switching into use resistors 374 in the fat channel 340.

(3) As a means of applying total corrections to individual components. Each component can be corrected for effects of all other components by using water-only corrections, e.g. equally accurate results have been achieved for fat using water correction as with the protein and lactose corrections applied separately.

An instrument user requiring fat-only readout could therefore obtain a faster rate of sampling using the fat/water correction combination. Also, in cases where fat and solids non-fat or fat and total solids results are required by the user who is able to tolerate slightly less accurate solids measurements, this method would be preferred. It should be explained that in order to obtain corrections for displacement rather than absorption effects, the infrared filters are reversed in the optical system, i.e. the water absorption filter is placed in the reference beam and the reference filter is placed in the measuring beam. There is no doubt that for some milk product analysis applications the water channel will be used to good effect.

Constants e, j, p and r are not required when the instrument is set up for analysis of whole milk. It is, however, visualized that for certain applications to milk product analysis, it may be necessary to include an intercept adjustment. In such cases this can be effected in fat, protein, lactose and water channels by adjustments to resistors 406,408,410 and 412. The value of these constants or intercepts will be indicated by the calibration data for the appropriate component.

With all adjustments made, the embodiment of the invention hereinabove described is now ready for operation. Referring to FIGS. 1–4, a specimen of milk to be sampled as in cup 149 in FIG. 2 is located beneath homogenizer inlet tube 146. Pump 144 is then activated to provide eleven pulses of milk from the specimen through homogenizer 142 to purge the sample cell 66 and the lines connecting the homogenizer to the sample cell. After the twelfth pulse from homogenizer 142, which places a specimen to be tested within the sample cell, pump operation is automatically terminated. Filter drum 72 is then activated sequentially to stop at the fat, protein, lactose and water positions. In the fat position, reference and measurement beams are alternately directed through the sample cell 66 onto the detector 70 which, in turn, operates servomotor 48 to position comb 60 within reference beam 30 (FIG. 1) until the reference and measurement beams seen by the photocell are equal in intensity. The signal on resistor 290 (FIG. 3) indicative of fat concentration is then stored on capacitor 342 (FIG. 14a). This process is repeated in the protein, lactose and water positions of filter drum 72. Corrected fat, protein and lactose concentrations in percent are then displayed at 316–320. If water display is desired, switch 422 (FIG. 14c) is placed in the position indicated and percent water concentration is displayed at 322. If total solids or solids non-fat are desired, switch 422 is placed in the alternative position and switch 430 is placed in the desired position such that percentage of total solids or solids non-fat is automatically provided at display 322. The specimen at 149 may then be changed and the cycle repeated as desired.

The invention claimed is:

1. Apparatus for quantitative analysis of optical characteristics of fluent materials comprising a source of radiation in the infrared spectrum, first means for splitting radiation from said source into first and second convergent beams, a drum disposed to rotate about a fixed axis and having a circumferential rim portion disposed to intersect one of said beams as said drum is rotated and an axial disc portion disposed to intersect the other of said beams as said drum is rotated, an optically transparent cell aligned with said first beam for holding a test sample, chopper means disposed between said drum and said cell and adapted to alternate between a first position in which said first beam is directed through said cell and a second position in which said second beam is directed through said cell, optical filter means disposed in said disc and rim portions of said drum as to intersect respective ones of said beams such that said chopper means alternately directs first and second beams through said cell at wavelengths corresponding to said filter means in said first and second positions of said chopper means, and energy responsive means disposed to be responsive to radiation transmitted through said cell for indicating an optical characteristic of a test sample within said cell.

2. The apparatus set forth in claim 1 wherein said rim is substantially cylindrical and said disc portion is perpendicular to said rim portion, and wherein said first and second beams are orthogonally convergent after passage through said filter means.

3. The apparatus set forth in claim 2 wherein said cell is disposed on axis with one of said first and second beams, and wherein said chopper means comprises a rotatable disc disposed at the zone of intersection of said first and second beams and having a first transparent circumferential portion for passing said first beam to said cell and a second reflective circumferential portion angulated to reflect the other of said first and second beams on axis to said cell.

4. The apparatus set forth in claim 3 wherein said filter means comprise first and second series of optical filters respectively disposed in said rim and disc portions of said drum with filters in said first and second series being grouped in coordinated pairs on radii from the radiation axis of said drum such that filters in said pairs simultaneously intersect associated ones of said first and second beams.

5. The apparatus set forth in claim 4 for quantitative analysis of a multiplicity of optical characteristics of a test sample contained in said cell, each said filter pair comprising a reference filter and a measurement filter for passing light to said cell at differing preselected wavelengths such that one of said characteristics is manifested by a difference in energy absorption at said differing wavelengths, wherein said light responsive means includes circuit means responsive to said difference in energy absorption for measuring said one characteristic.

6. The apparatus set forth in claim 5 further comprising means for step-wise rotation of said drum for locating each of said filter pairs in said beam, said circuit means being responsive to differences in energy absorption at the said differing wavelengths of each said filter pair for measuring each said characteristic, and control means coupled to said drum for controlling said circuit means as a function of the filter pair intersecting said beams.

7. The apparatus set forth in claim 6 further comprising adjustable first energy shutter means disposed to intersect one of said beams, and means coupled to said control means for adjustably positioning said first shutter means within said one beam at a position selected for each said filter pair to provide a zero indication of optical characteristics at said radiation responsive means in the absence of a sample in said cell.

8. The apparatus set forth in claim 6 wherein said filter means comprises first and second series of absorption filters each selected to transmit radiation in a band around a selected nominal peak wavelength, said first and second series being adapted to transmit wavelengths in a selected range of the infrared spectrum, and wherein said radiation source includes interference filter means for transmitting to said absorption filters substantially only energy within said range so as to minimize heating of said absorption filters.

9. The apparatus set forth in claim 6 for measuring fat, protein and lactose concentrations in milk wherein said reference and measurement filters are grouped in pairs having respective nominal peak transmission wavelengths of about $3.47\mu$ and $3.418\mu$ for fat, $6.68\mu$ and $6.46\mu$ for protein, and $7.67\mu$ and $9.6\mu$ for lactose.

10. The apparatus set forth in claim 9 for further measuring water concentration in milk wherein said reference and measurement filters are grouped in an additional pair possessing respective nominal peak transmission wavelengths of about $5.55\mu$ and $4.7\mu$ for measurement of water concentration.

11. In an apparatus for quantitative analysis of optical characteristics of materials comprising an infrared source, an optically transparent cell for holding a test sample, means for splitting energy from said source into first and second beams, means for alternately directing said first and second beams through said cell, energy responsive means disposed to receive radiation transmitted through said cell alternately in said first and second beams, and radiation filter means disposed to intersect said first and second beams such that radiation incident on said energy responsive means in said first and second beams exhibit differing wavelength characteristics, the improvement wherein said beam splitting means comprises means for splitting said beam into a said first beam on a first axis which intersects said cell and energy responsive means, and a said second beam on a second axis orthogonally intersecting said first axis, wherein said filter means comprises rotatable means having first and second series of filters disposed in orthogonal pairs and means for stepwise rotation of said rotatable means such that selected ones of said first and second filter series comprising said pairs are alternately positioned to intersect said first and second beams, and wherein said means for alternately directing said beams through said cell comprises a chopper having a transparent portion and a reflective portion, means positioning said chopper at the area of intersection of said first and second axes at an orientation of 45° with respect to both said axes, and means for rotating said chopper such that, in alternation, said first beam is transmitted by said transparent portion to said cell and said second beam is reflected by said second portion to said cell.

12. The apparatus set forth in claim 11 wherein said first and second beams are substantially confocal at said cell.

13. The apparatus set forth in claim 12 wherein said beam splitting means comprise first and second plane mirrors reflecting light from said source, a first spherical mirror disposed to receive said first beam from said first plane mirror and to focus said first beam at said cell, and a second spherical mirror disposed to receive said second beam from said second plane mirror and to cooperate with said reflective position of said disc to focus said second beam at said cell, and wherein said apparatus further comprises an ellipsoidal mirror having a first focus at said cell and a second focus at said light responsive means.

14. The apparatus set forth in claim 11 wherein said energy responsive means comprises thermoelectric means disposed such that first and second beams are alternately incident thereon, shutter means adapted to be adjustably positioned in one of said first and second beams, servo means coupled to said thermoelectric means and responsive to differing intensity of said first and second beams alternately incident on said thermoelectric means for adjustably positioning said shutter means in said one of said beams until said intensities are equal, and means responsive to said servo means for indicating said optical characteristics.

15. The apparatus set forth in claim 14 wherein said servo means comprises a pivot arm carrying said shutter means, a servo motor electrically connected to said light responsive means, transmission means coupling said pivot arm to said motor, and a coil spring coupled to said pivot arm for biasing said pivot arm and said transmission means against said motor such that said motor exhibits substantially zero backlash.

16. Apparatus for spectrophotometric absorption analysis of material comprising a source of infrared radiation means including means for generating first and second divergent beams from said source, a cell for holding a test sample of material, first reflective means disposed in the path of said first beam for focusing said first beam at said cell on an optical axis, detection means, ellipsoidal reflective means having a first focus at said cell and a second focus at said detection means, second reflective means disposed in the path of said second beam for redirecting said second beam to intersect said first beam orthogonally to said axis and to focus said second beam, means disposed at the zone of intersection of said first and second beams for alternately and sequentially directing said first and second beams through said cell such that said second beam is substantially confocal with said first beam when directed through said cell, filter means having a first portion disposed to intersect said first beam between said first reflective means and said means for alternately directing said beams through said cell, a second portion orthogonal to said first portion and disposed to intersect said second beam between said second reflective means and said means for alternately directing said beams, first and second series of optical filters respectively disposed on said first and second portions in coordinated pairs such that filters in said pairs simultaneously intersect said first and second beams and means for alternately locating selected one of said filter pairs in said beams, and means coupled to said detection means and responsive to differing intensity of beams passing through each said filter pair and through said cell for measuring optical characteristics of the test sample.

17. Apparatus for optically analyzing fluid emulsions such as milk which comprises an optically transparent cell for holding a sample of said emulsion of predetermined quantity, means including a homogenizer having an inlet to receive said fluid emulsion and an outlet for providing a quantity of homogenized fluid substantially in excess of said predetermined quantity, first conduit means for directing fluid from said homogenizer through said sample cell, second conduit means operatively connected to said first conduit means upstream of said cell for routing fluid to bypass said cell, control means coupled to said homogenizer means, said first conduit means and said second conduit means for directing a first measured quantity of homogenized fluid through said first conduit means and said second conduit means bypassing said cell so as to purge said homogenizer and said first conduit means and then for directing a second measured quantity of homogenized fluid through said first conduit means to said cell, and means responsive to said control means for directing an optical beam through said cell so as to analyze fluid in said cell for a selected optical characteristic.

18. The apparatus set forth in claim 17 wherein said control means comprises a first control valve disposed in one of said first and second conduit means and operate when open to permit passage of fluid through the associated said conduit means, and means for closing said control valve for directing fluid through the other of said conduit means.

19. The apparatus set forth in claim 18 wherein said control means further comprises a second control valve disposed in the said other of said conduit means, said second control valve including means normally closing said second control valve so as to resist passage of said fluid through said other conduit means when said first control valve is open and means responsive to increase in pressure in said other conduit means when said first control valve is closed to open said second control valve.

20. The apparatus set forth in claim 19 wherein said homogenizer includes two valves and a hydraulic diaphragm pump for receiving and directing fluid emulsion through said valves, wherein said means including said homogenizer includes means for providing pulsed hydraulic energy to said diaphragm pump such that said quantity of fluid appears in pulses, and wherein said control means further comprises means coupled to said pulsed hydraulic energy providing means and to said first control valve for directing a series of first pulses through said first and second means bypassing said cell for purging said first conduit means and a series of second pulses through said first conduit means both to purge said cell and to fill said cell with filtered fluid to be analyzed.

21. The apparatus set forth in claim 20 wherein said cell comprises a pair of opposed windows separated by a space for holding test material, and wherein said first and second conduit means are of resilient tubular construction for elastically absorbing impulse fluid pressure from said homogenizer and thereby preventing flexure of said cell windows.

22. The apparatus set forth in claim 21 wherein said second series of pulses comprises one pulse of emulsion substantially in excess of that needed to fill said cell.

23. The apparatus set forth in claim 22 for analyzing milk further comprising means mounted to said homogenizer for heating said homogenizer to a temperature above room temperature.

24. The apparatus set forth in claim 23 wherein said temperature is substantially 40° C.

25. The apparatus set forth in claim 17 further comprising filter means disposed at the junction of said first and second conduit means, such that said second measured quantity of fluid flowing through said first conduit means to said cell passes through and is filtered by said filter means, while said first measured quantity of fluid flowing through said first and second conduit means bypasses and tends to wash said filter means.

26. The apparatus set forth in claim 17 wherein said sample cell comprises a pair of flat parallel optical windows and means spacing said windows from each other to provide a generally planar sample zone, fluid inlet and outlet ports including openings extending through one of said windows and spaced from each other such that fluid entering said inlet port traverses said zone between said windows before exiting said outlet port, a fluid passage extending past said inlet port and connecting with said inlet port through an opening in a side wall of said passage, and a filter medium carried against said passage side wall across said opening such that fluid which enters said zone through said inlet port is filtered by said filter medium while fluid passing through said passage past said inlet port tends to wash said filter medium.

27. The apparatus set forth in claim 26 wherein said cell further comprises a plate having a flat surface carried in facing engagement with the other of said windows externally of said zone, passages extending through said other window and opening into said zone, and a groove in said flat plate surface in fluid communication with said passages in said other window such that a quantity of fluid entering said zone through said inlet port bypasses said zone by passing through said passages in said other window and through said groove.

28. The apparatus set forth in claim 27 wherein said plate has a central opening for passage of an optical beam through said windows, wherein said groove is generally circular surrounding said opening in said plate, and wherein said passages in said other window are substantially aligned with said openings extending through said one window.

* * * * *